(12) United States Patent
Sugiyama et al.

(10) Patent No.: US 9,500,600 B2
(45) Date of Patent: Nov. 22, 2016

(54) RADIATION IMAGE ACQUISITION SYSTEM

(71) Applicant: HAMAMATSU PHOTONICS K.K., Hamamatsu-shi, Shizuoka (JP)

(72) Inventors: Mototsugu Sugiyama, Hamamatsu (JP); Toshiyasu Suyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 122 days.

(21) Appl. No.: 14/415,273

(22) PCT Filed: Jun. 18, 2013

(86) PCT No.: PCT/JP2013/066742
§ 371 (c)(1),
(2) Date: Jan. 16, 2015

(87) PCT Pub. No.: WO2014/013829
PCT Pub. Date: Jan. 23, 2014

(65) Prior Publication Data
US 2015/0185165 A1    Jul. 2, 2015

(30) Foreign Application Priority Data

Jul. 20, 2012 (JP) .................... 2012-161919

(51) Int. Cl.
*G01N 23/04* (2006.01)
*G01T 1/20* (2006.01)

(52) U.S. Cl.
CPC .............. *G01N 23/04* (2013.01); *G01T 1/20* (2013.01); *G01N 2223/3306* (2013.01);
(Continued)

(58) Field of Classification Search
CPC ............ G01N 23/04; G01T 1/20; G01T 1/2002; G01T 1/2006; G01T 1/2008;
(Continued)

(56) References Cited

U.S. PATENT DOCUMENTS 4,578,803 A * 3/1986 Macovski ............ G01N 23/043
378/156
5,864,146 A * 1/1999 Karellas ............... A61B 6/4258
250/581

(Continued)

FOREIGN PATENT DOCUMENTS

CN        101371787      9/2010
CN        101836867      9/2010
(Continued)

OTHER PUBLICATIONS

International Preliminary Report on Patentability dated Jan. 20, 2015 for PCT/JP2013/066742.

*Primary Examiner* — David A Vanore
(74) *Attorney, Agent, or Firm* — Drinker Biddle & Reath LLP

(57) ABSTRACT

A radiation image acquisition system of an aspect of the present invention includes a radiation source emitting radiation toward an object, a holding unit holding the object, a wavelength conversion member generating scintillation light in response to incidence of the radiation emitted from the radiation source and transmitted through the object, a first imaging means condensing and imaging scintillation light emitted from an incidence surface of the radiation of the wavelength conversion member, a second imaging means condensing and imaging scintillation light emitted from a surface opposite to the incidence surface of the wavelength conversion member, a holding unit position adjusting means adjusting the position of the holding unit between the radiation source and the wavelength conversion member, and an imaging position adjusting means adjusting the position of the first imaging means.

17 Claims, 12 Drawing Sheets

(52) U.S. Cl.
CPC . *G01N 2223/3308* (2013.01); *G01N 2223/424* (2013.01); *G01N 2223/505* (2013.01); *G01N 2223/6113* (2013.01)

(58) Field of Classification Search
CPC ............... G01T 3/06; G21K 4/00; G21K 1/00; G21K 1/10
USPC ............ 378/62, 156, 205, 208, 79, 98.8; 250/362, 363.01, 366, 484.2, 581, 582
See application file for complete search history.

(56) References Cited

U.S. PATENT DOCUMENTS

| | | | |
|---|---|---|---|
| 7,130,375 B1* | 10/2006 | Yun et al. | ............... G01N 23/04 378/205 |
| 7,405,406 B1* | 7/2008 | Nagarkar | ............... G01T 1/2018 250/366 |
| 9,255,996 B2* | 2/2016 | Sugiyama | ............... G01N 23/04 |
| 9,268,039 B2* | 2/2016 | Sugiyama | ................. G01T 1/20 |
| 9,279,890 B2* | 3/2016 | Sugiyama | ............... G01N 23/04 |
| 2014/0016752 A1* | 1/2014 | Sugiyama | ............... G01N 23/04 378/62 |
| 2014/0016753 A1* | 1/2014 | Sugiyama | ............... G01N 23/04 378/62 |
| 2014/0016754 A1* | 1/2014 | Sugiyama | ................. G01T 1/20 378/62 |
| 2014/0021372 A1* | 1/2014 | Suyama | .................... G21K 4/00 250/484.2 |
| 2015/0185165 A1* | 7/2015 | Sugiyama | ............... G01N 23/04 378/62 |
| 2016/0103231 A1* | 4/2016 | Sugiyama | ............... G01N 23/04 250/362 |

FOREIGN PATENT DOCUMENTS

| | | |
|---|---|---|
| CN | 101937095 | 1/2011 |
| JP | H05-312734 | 11/1993 |
| JP | 7-27866 A | 1/1995 |
| JP | H11-211677 A | 8/1999 |
| JP | 2000-039407 A | 2/2000 |
| JP | 2000-510729 A | 8/2000 |
| JP | 2007-155653 | 6/2007 |
| WO | WO 2011/093127 | 8/2011 |
| WO | WO-2012/101879 A1 | 8/2012 |
| WO | WO-2012/101880 A1 | 8/2012 |
| WO | WO-2012/101883 A1 | 8/2012 |

* cited by examiner (a)

(b)

(c)

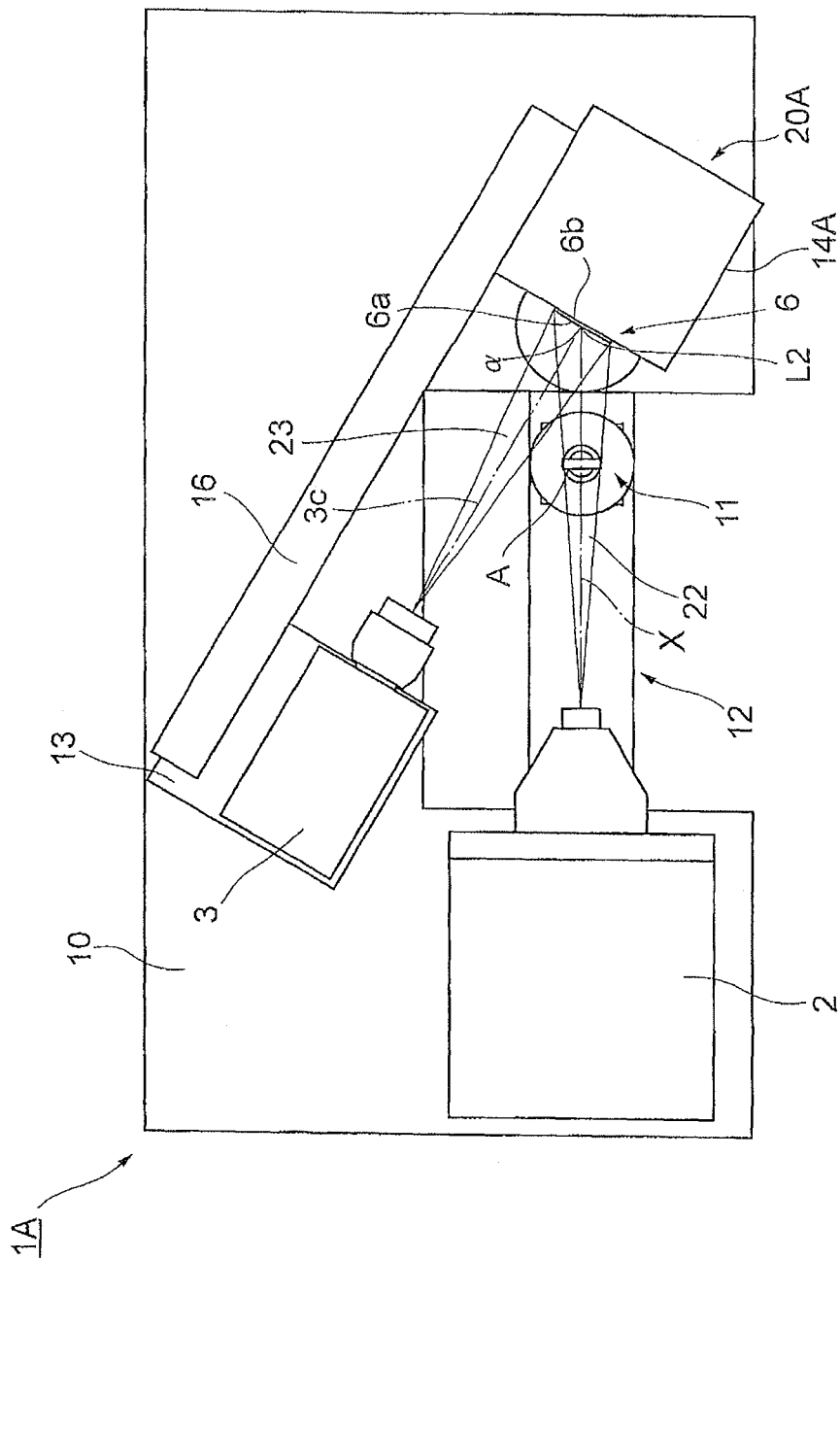

RADIATION IMAGE ACQUISITION SYSTEM

TECHNICAL FIELD

The present invention relates to a radiation image acquisition system.

BACKGROUND ART

Conventionally, as described in the following Patent Document 1, there is known a device which irradiates a tabular scintillator with X-rays emitted from an X-ray source and transmitted through an imaging object, detects visible light (scintillation light) generated in the scintillator by solid-state photodetectors laminated on both surfaces of the scintillator, and superimposes image signals output from the respective solid-state photodetectors on each other to acquire a radiation image. In this device, photodetecting elements are coupled to an X-ray incidence surface of the scintillator and its back surface, and the detection efficiency for visible light is enhanced by detecting visible light in each of the photodetecting element on the incidence surface side and the photodetecting element on the back surface side.

Also, as described in the following Patent Document 2, there is known a device which, by use of two scintillators overlaid with each other and one detector, detects scintillation light emitted from the scintillator on an incidence surface side by one surface of the detector, and detects scintillation light emitted from the scintillator on the opposite side by the other surface of the detector. In this device, images are formed with two types of different wavelengths on the respective surfaces of the detector.

CITATION LIST

Patent Literature

Patent Document 1: Japanese Patent Application Laid-Open No. H07-27866
Patent Document 2: Japanese Translation of International Application No. 2000-510729

SUMMARY OF INVENTION

Technical Problem

Meanwhile, because the X-ray source is a spot light source, it is necessary for the object to be disposed in at least a region that is irradiated with X-rays. For example, when the object to be imaged is large, and a full picture of the object is desired to be captured, it is necessary to dispose the object at a position closer to the scintillator. By bringing the object close to the scintillator, the projection magnification ratio with respect to the scintillator can be lowered, which allows having a full picture of the object within the range of the scintillator.

The present inventors have diligently studied a radiation image acquisition system including a first imaging means that condenses and images scintillation light emitted from an X-ray incidence surface of a scintillator and a second imaging means that condenses and images scintillation light emitted from a surface opposite to the incidence surface. In such a radiation image acquisition system, the first imaging means, i.e., the imaging means on the incidence surface side is located on the same side as that of the object with reference to the scintillator.

When the object is brought close to the scintillator in order to adjust the magnification ratio as described above, the object sometimes enters the field of view of the imaging means on the incidence surface side. If the object enters the field of view of the imaging means on the incidence surface side, for example, vignetting due to the object is produced in an image. Therefore, a radiation image acquisition system capable of preventing an object from entering the field of view of the imaging means on the incidence surface side while acquiring an image at a desired magnification ratio has been demanded.

It is an object of the present invention to provide a radiation image acquisition system capable of preventing an object from entering the field of view of the imaging means on the incidence surface side while acquiring an image at a desired magnification ratio.

Solution to Problem

A radiation image acquisition system of an aspect of the present invention is characterized by including a radiation source emitting radiation toward an object, a holding unit holding the object, a wavelength conversion member generating scintillation light in response to incidence of the radiation emitted from the radiation source and transmitted through the object, a first imaging means condensing and imaging scintillation light emitted from an incidence surface of the radiation of the wavelength conversion member, a second imaging means condensing and imaging scintillation light emitted from a surface opposite to the incidence surface of the wavelength conversion member, a holding unit position adjusting means adjusting the position of the holding unit between the radiation source and the wavelength conversion member, and an imaging position adjusting means adjusting the position of the first imaging means.

According to this radiation image acquisition system, scintillation lights emitted from the radiation incidence surface of the wavelength conversion member and its opposite surface are respectively condensed and imaged by the first imaging means and the second imaging means. The first imaging means is an imaging means on the incidence surface side, and the second imaging means is an imaging means on the side opposite to the incidence surface. By adjusting the position of the holding unit between the radiation source and the wavelength conversion member by the holding unit position adjusting means, the object can be brought close to the wavelength conversion member or moved away from the wavelength conversion member. By bringing the object close to the wavelength conversion member, the magnification ratio can be lowered. By moving the object away from the wavelength conversion member and bringing the object close to the radiation source, the magnification ratio can be increased. Here, even when the object is brought close to the wavelength conversion member, by adjusting the position of the first imaging means by the imaging position adjusting means, entry of the object into the field of view of the first imaging means can be prevented. Thus, entry of the object into the field of view of the first imaging means being an imaging means on the incidence surface side is prevented, while an image can be acquired at a desired magnification ratio.

The imaging position adjusting means rotates the first imaging means with a point where an optical axis of the first imaging means and the incidence surface of the wavelength conversion member cross each other set as a rotation center. According to this arrangement, even when the position of the first imaging means is adjusted, the optical path length from the wavelength conversion member to the first imaging means does not change. Accordingly, correction to an image becomes easy.

The imaging position adjusting means keeps an angle created by the optical axis of the first imaging means and the incidence surface of the wavelength conversion member while rotating the first imaging means and the wavelength conversion member. According to this arrangement, even when the position of first imaging means is adjusted, the angle created by the optical axis of the first imaging means and the incidence surface of the wavelength conversion member is kept fixed, and thus correction to an image becomes even easier. Also, it is not necessary to frequently perform calibration in the first imaging means, so that the convenience is improved.

The imaging position adjusting means keeps an angle created by an optical axis of the second imaging means and the opposite surface of the wavelength conversion member while rotating the first imaging means, the wavelength conversion member, and the second imaging means. According to this arrangement, the first imaging means, the wavelength conversion member, and the second imaging means integrally rotate with the point described above set as a rotation center. Accordingly, even when the position of the first imaging means and the second imaging means is adjusted, the relative positional relationship of the first imaging means, the wavelength conversion member, and the second imaging means does not change. Therefore, images for which an inter-image operation is easily performed can be captured. Also, it is not necessary to frequently perform calibration in the second imaging means, so that the convenience is improved.

The above-described radiation image acquisition system includes a detecting means detecting whether the object is in a field of view of the first imaging means. According to this arrangement, because whether the object is in the field of view of the first imaging means is detected by the detecting means, the occurrence of "vignetting" in an image can be reliably prevented.

The detecting means detects whether the object is in the field of view of the first imaging means based on a first image captured by the first imaging means and a second image captured by the second imaging means. According to this arrangement, whether the object is in the field of view of the first imaging means can be accurately detected.

The detecting means detects whether the object is in the field of view of the first imaging means based on a difference in light intensity between the first image and the second image. According to this arrangement, whether the object is in the field of view of the first imaging means can be accurately detected.

The detecting means detects whether the object is in the field of view of the first imaging means based on a difference image between the first image and the second image. According to this arrangement, whether the object is in the field of view of the first imaging means can be accurately detected.

The detecting means detects whether the object is in the field of view of the first imaging means based on a ratio of brightness between the first image and the second image. According to this arrangement, whether the object is in the field of view of the first imaging means can be accurately detected.

The detecting means detects whether the object is in the field of view of the first imaging means based on successive images successively captured by the first imaging means while the holding unit is moved by the holding unit position adjusting means. According to this arrangement, the point in time where the object has slipped out of the field of view of the first imaging means or the point in time where the object has entered the field of view of the first imaging means can be accurately detected. As a result, the inclination angle of the wavelength conversion member with respect to the radiation source can be minimized, so that an image with little perspective is easily acquired.

The above-described radiation image acquisition system includes an image operating means performing an image operation of a first image captured by the first imaging means and a second image captured by the second imaging means based on a rotation angle of the first imaging means, the wavelength conversion member, and the second imaging means. According to this arrangement, a CT (Computed Tomography) image of the object can be acquired.

Advantageous Effects of Invention

According to an aspect of the present invention, entry of an object into the field of view of the first imaging means being an imaging means on the incidence surface side can be prevented, while an image can be acquired at a desired magnification ratio.

BRIEF DESCRIPTION OF DRAWINGS

FIG. 12 is a plan view of the radiation image acquisition system of FIG. 10.

DESCRIPTION OF EMBODIMENTS

Figure 1:
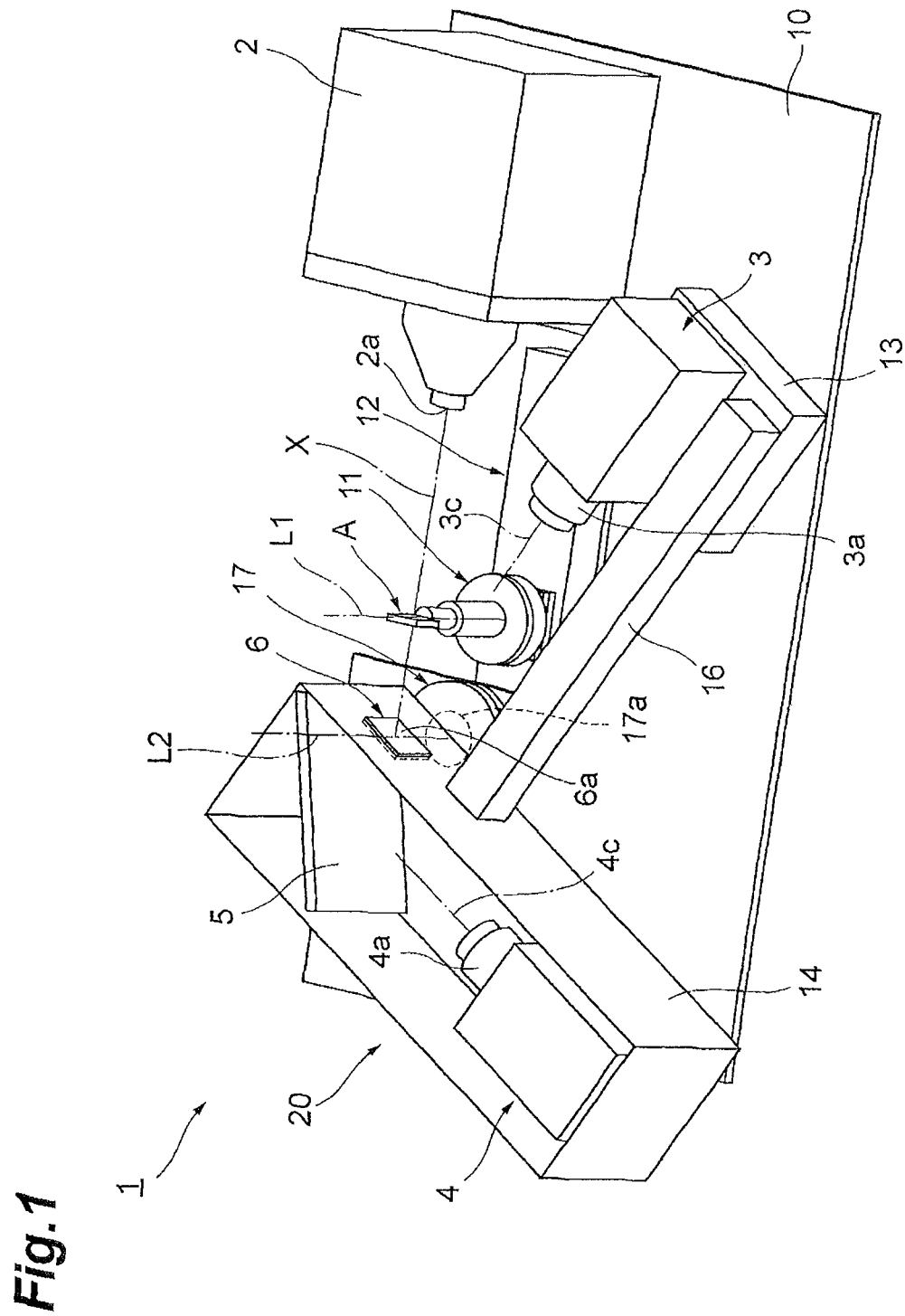
FIG. 1 is a perspective view of a radiation image acquisition system according to a first embodiment of the present invention.

Hereinafter, an embodiment of the present invention will be described with reference to the drawings. In addition, the same elements will be denoted by the same reference signs in the description of the drawings, and overlapping description will be omitted. Also, the respective drawings are prepared for the purpose of description, and are drawn so that the portions to be described are especially emphasized. Therefore, the dimensional ratios of respective members in the drawings are not always coincident with actual ratios.

Figure 2:
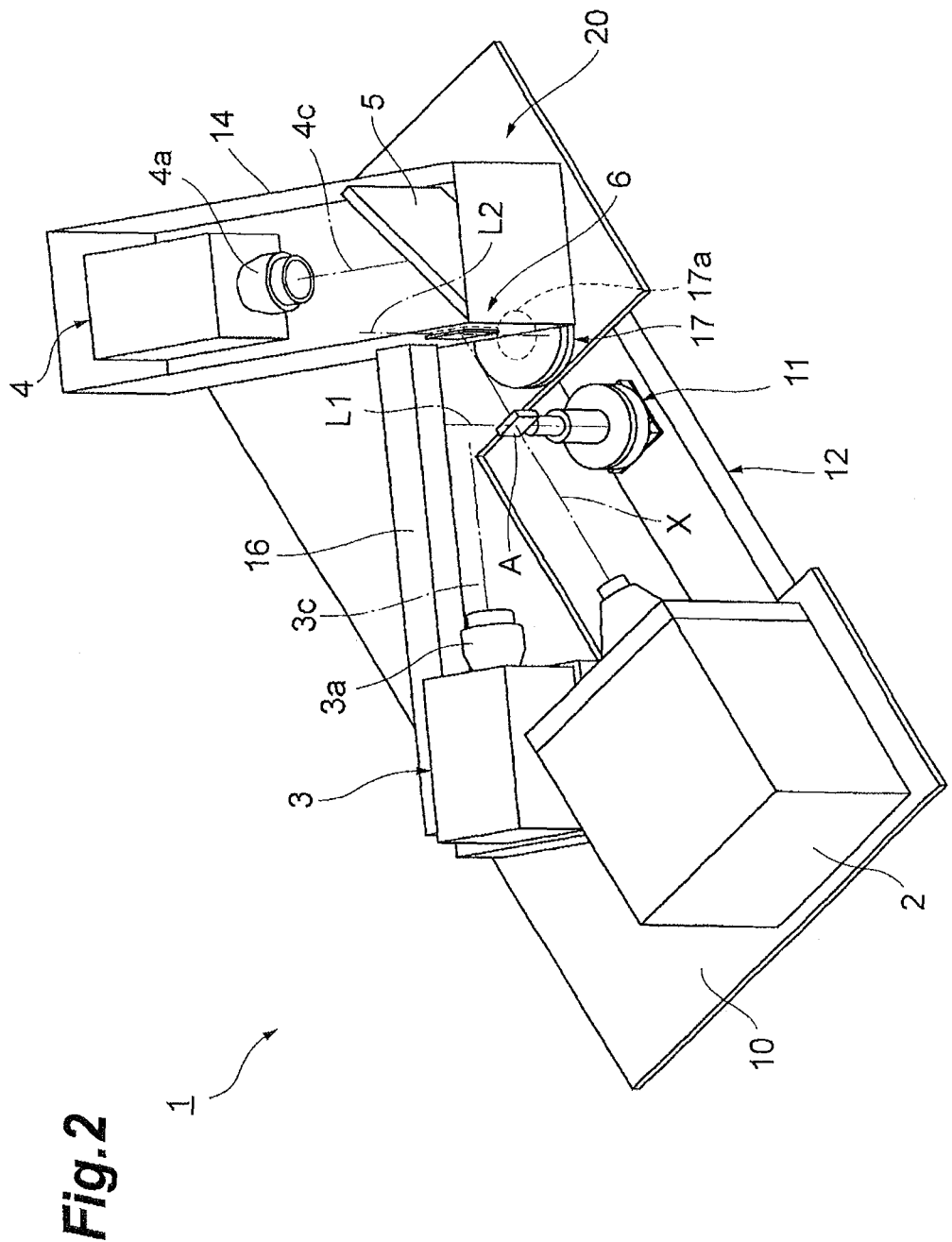
FIG. 2 is a perspective view of the radiation image acquisition system of FIG. 1 from another angle.
Figure 3:
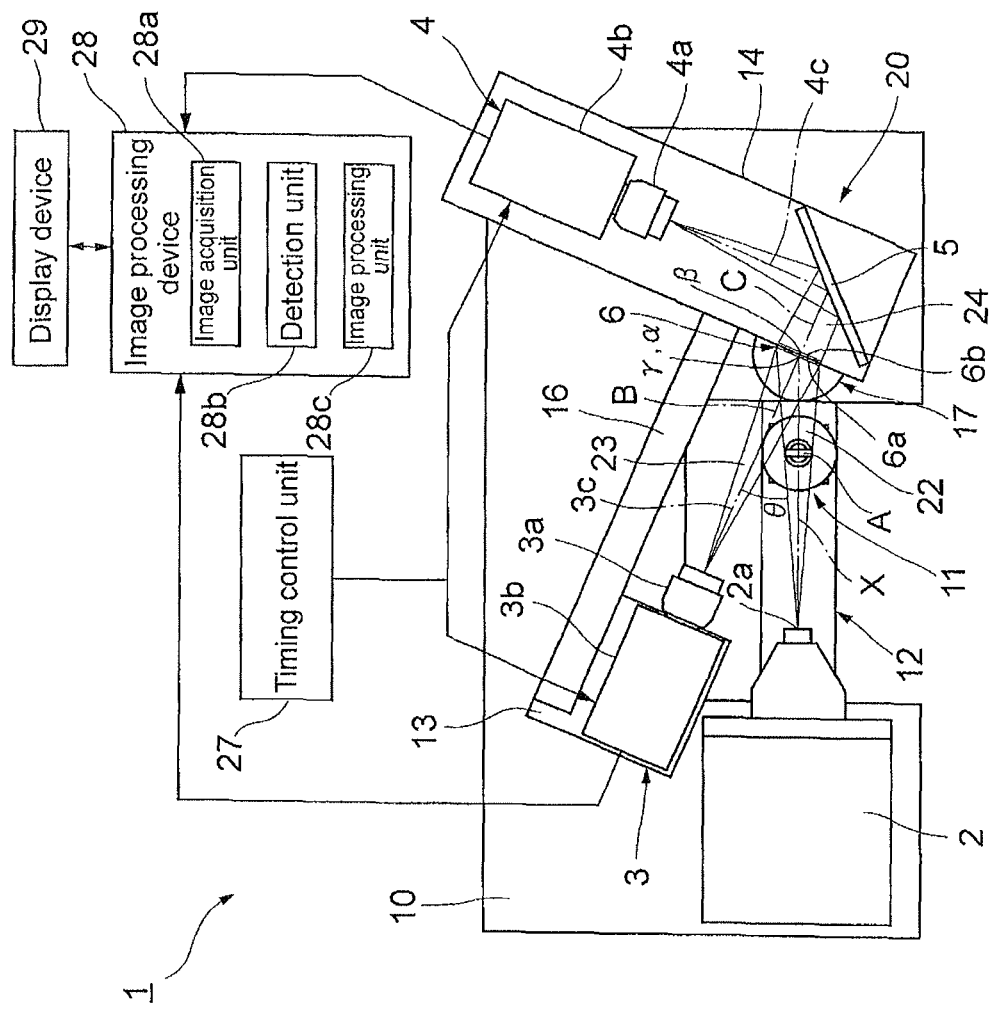
FIG. 3 is a plan view of the radiation image acquisition system of FIG. 1.

As shown in FIG. 1 to FIG. 3, a radiation image acquisition system 1 of a first embodiment is a system for acquiring a radiation image of an object A. The radiation image acquisition system 1 includes a radiation source 2 that emits radiation such as white X-rays toward the object A, a wavelength conversion plate (wavelength conversion member) 6 that generates scintillation light in response to incidence of the radiation emitted from the radiation source 2 and transmitted through the object A, a front observation photodetector (first imaging means) 3 that condenses and images scintillation light emitted from a radiation incidence surface 6a of the wavelength conversion plate 6, and a back observation photodetector (second imaging means) 4 that condenses and images scintillation light emitted from a back surface 6b (refer to FIG. 3) that is a surface opposite to the incidence surface 6a.

The radiation source 2 emits cone beam X-rays from an X-ray emission spot 2a. The object A is an electronic component such as a semiconductor device, and is, for example, a semiconductor integrated circuit. The object A is not limited to a semiconductor device, and may be food or the like. The object A may even be a film or the like. The radiation image acquisition system 1 acquires a radiation image of the object A for the purpose of, for example, a non-destructive analysis of an industrial product.

The wavelength conversion plate 6 is a tabular wavelength conversion member, and is, for example, a scintillator such as $Gd_2O_2S$:Tb, $Gd_2O_2S$:Pr, CsI:Tl, $CdWO_4$, $CaWO_4$, $Gd_2SiO_5$:Ce, $Lu_{0.4}Gd_{1.6}SiO_5$, $Bi_4Ge_3O_{12}$, $Lu_2SiO_5$:Ce, $Y_2SiO_5$, $YAlO_3$:Ce, $Y_2O_2S$:Tb, or $YTaO_4$:Tm. The thickness of the wavelength conversion plate 6 is, in a range of several micrometers to several millimeters, set to an appropriate value according to the energy band of detecting radiation.

The wavelength conversion plate 6 converts X-rays transmitted through the object A to visible light. X-rays with relatively low energy are converted by the incidence surface 6a that is a front surface of the wavelength conversion plate 6, and is emitted from the incidence surface 6a. Also, X-rays with relatively high energy are converted by the back surface 6b of the wavelength conversion plate 6, and is emitted from the back surface 6b.

The front observation photodetector 3 (hereinafter, referred to as a "front surface detector 3") is an imaging means according to an indirect conversion method that captures a projection image (i.e., a radiation transmission image) of the object A projected on the wavelength conversion plate 6 from the side of the incidence surface 6a of the wavelength conversion plate 6. That is, the front surface detector 3 is an imaging means on the side of the incidence surface 6a. The front surface detector 3 has a condenser lens unit 3a that condenses scintillation light emitted from the incidence surface 6a of the wavelength conversion plate 6, and an imaging unit 3b that images scintillation light condensed by the condenser lens unit 3a. The front surface detector 3 is a lens coupling type detector. The condenser lens unit 3a condenses scintillation light in a field of view 23. As the imaging unit 3b, for example, an area sensor such as a CMOS sensor or a CCD sensor is used.

The back observation photodetector 4 (hereinafter, referred to as a "back surface detector 4" is an imaging means according to an indirect conversion method that captures a projection image (i.e., a radiation transmission image) of the object A projected on the wavelength conversion plate 6 from the side of the back surface 6b of the wavelength conversion plate 6. That is, the back surface detector 4 is an imaging means on the side of the back surface 6b. The back surface detector 4 has a condenser lens unit 4a that condenses scintillation light emitted from the back surface 6b of the wavelength conversion plate 6, and an imaging unit 4b that images scintillation light condensed by the condenser lens unit 4a. The back surface detector 4 is a lens coupling type detector, and has the same configuration as that of the front surface detector 3 described above. The condenser lens unit 4a condenses scintillation light in a field of view 24 via a mirror 5. As the imaging unit 4b, for example, an area sensor such as a CMOS sensor or a CCD sensor is used.

The mirror 5 reflects light emitted from the back surface 6b of the wavelength conversion plate 6, and directs the reflected light toward the back surface detector 4. Exposure to radiation of the back surface detector 4 can thereby be prevented.

As shown in FIG. 3, the radiation image acquisition system 1 includes a timing control unit 27 that controls imaging timing in the front surface detector 3 and the back surface detector 4, an image processing device 28 that is input with image signals output from the front surface detector 3 and the back surface detector 4, and executes a predetermined processing such as an image processing based on the respective input image signals, and a display device 29 that is input with image signals output from the image processing device 28, and displays a radiation image. The timing control unit 27 and the image processing device 28 are constructed by a computer having a CPU (Central Processing Unit), a ROM (Read-Only Memory), a RAM (Random-Access Memory), an input/output interface, etc. As the display device 29, a publicly known display is used. In addition, the timing control unit 27 and the image processing device 28 may be constructed as programs to be executed by a single computer, or may be constructed as units that are separately provided.

The image processing device 28 has an image acquisition unit 28a, a detection unit (detecting means) 28b, and an image processing unit (image operating means) 28c. The image acquisition unit 28a is input with image signals output from the front surface detector 3 and the back surface detector 4. The detection unit 28b detects whether the object A is within the field of view 23 of the front surface detector 3 based on a radiation image indicated in the image signals input by the image acquisition unit 28a. The image processing unit 28c executes a predetermined processing such as an inter-image operation including a difference operation and an addition operation based on the image signals input by the image acquisition unit 28a. The image processing unit 28c outputs image signals after the image processing to the display device 29.

As shown in FIG. 1 to FIG. 3, the radiation source 2, the front surface detector 3, the back surface detector 4, and the wavelength conversion plate 6 described above are mounted on a plate-like base 10. On one end portion of the base 10, the radiation source 2 is placed, and fixed. The radiation source 2 has an optical axis X parallel to an extending direction of the base 10. On the optical axis X of the radiation source 2, the object A and the wavelength conversion plate 6 are disposed. That is, the object A is disposed between the X-ray emission spot 2a of the radiation source 2 and the wavelength conversion plate 6. The object A is held by a projection angle changing stage (holding unit) 11.

The projection angle changing stage 11 is for holding the object A and rotating the object A. Rotating the object A by the projection angle changing stage 11 allows acquiring radiation images with various projection angles. The projection angle changing stage 11 has a drive mechanism (not shown), and rotates the object A about a rotation axis L1 by the drive mechanism. The rotation axis L1 is perpendicular to the extending direction of the base 10. The rotation axis L1 intersects the optical axis X of the radiation source 2, and also passes substantially the center of the object A. In addition, the rotation axis L1 is not limited to the case of passing substantially the center of the object A, and may be located at a position deviated from the object A.

Further, the projection angle changing stage 11 is supported by a magnification ratio changing stage (holding unit position adjusting means) 12. The magnification ratio changing stage 12 is for moving the object A along the optical axis of the radiation source 2 between the radiation source 2 and the wavelength conversion plate 6. The magnification ratio changing stage 12 moves the object A to change the distance FOD (Focus-Object Distance) between the radiation source 2 (X-ray focus) and the object A, and thereby adjusts a ratio of FOD to the distance FID (Focus-Image Distance) between the radiation source 2 (X-ray focus) and the wavelength conversion plate 6. The magnification ratio of a radiation image can thereby be changed. The projection angle changing stage 12 is attached to the base 10, and extends parallel to the optical axis X of the radiation source 2. The magnification ratio changing stage 12 has a drive mechanism (not shown), and causes a sliding movement of the projection angle changing stage 11 between the radiation source 2 and the wavelength conversion plate 6 by the drive mechanism. The moving direction of the projection angle changing stage 11 is parallel to the optical axis X of the radiation source 2.

To the other end portion of the base 10, a rotating body 20 that is rotatable with respect to the base 10 is attached. The rotating body 20 is supported by a shooting angle changing stage (imaging position adjusting means) 17. The shooting angle changing stage 17 has a drive mechanism 17a, and rotates the rotating body 20 about a rotation axis L2 by the drive mechanism 17a. The rotation axis L2 is parallel to the rotation axis L1. The rotation axis L2 is perpendicular to the extending direction of the base 10. The rotation axis L2 intersects the optical axis X of the radiation source 2, and also passes over the incidence surface 6a of the wavelength conversion plate 6. Also, the rotation axis L2 intersects an optical axis 3c of the front surface detector 3. That is, the shooting angle changing stage 17 rotates the rotating body 20 with a point where the optical axis 3c of the front surface detector 3 and the incidence surface 6a of the wavelength conversion plate 6 cross each other (i.e., a point α to be described later) set as a rotation center.

The rotating body 20 has an X-ray protection box 14 that is supported by the shooting angle changing stage 17, a front surface camera mount 13 on which the front surface detector 3 is placed, and an interlocking arm 16 that interlocks the X-ray protection box 14 and the front surface camera mount 13.

The X-ray protection box 14 is a casing made of, for example, an X-ray shielding material such as lead, and houses the back surface detector 4. The X-ray protection box 14, by shielding X-rays emitted from the radiation source 2, prevents the back surface detector 4 from being exposed thereto. In a surface of the X-ray protection box 14 opposed to the radiation source 2, a quadrangular opening is formed. The wavelength conversion plate 6 is fitted in the opening to be fixed to the X-ray protection box 14.

To the interior of the X-ray protection box 14, the back surface detector 4 and the mirror 5 are fixed. The mirror 5 has a reflecting surface that is perpendicular to the extending direction of the base 10 and creates 45 degrees with respect to the back surface 6b of the wavelength conversion plate 6. The condenser lens unit 4a of the back surface detector 4 is opposed to the mirror 5. The back surface detector 4 has an optical axis 4c that is parallel to the extending direction of the base 10. The optical axis 4c of the back surface detector 4 is parallel to the back surface 6b of the wavelength conversion plate 6. That is, the optical axis 4c is perpendicular to the reflecting surface of the mirror 5. The mirror 5 reflects scintillation light emitted from the back surface 6b of the wavelength conversion plate 6, and directs this light toward the back surface detector 4. In addition, the angles of the mirror 5 and the optical axis 4c with respect to the back surface 6b of the wavelength conversion plate 6 are not limited to the angles described above, and can be appropriately set. It suffices with an arrangement which enables condensing scintillation light emitted from the back surface 6b of the wavelength conversion plate 6 by the back surface detector 4.

The interlocking arm 16 extends from the other end portion to the one end portion of the base 10. That is, the interlocking arm 16 extends from near a side of the wavelength conversion plate 6 in the X-ray protection box 14 to a side of the radiation source 2. The interlocking arm 16 is disposed at a position so as not to interfere with the optical axis X of the radiation source 2. On the front surface camera mount 13, the front surface detector 3 is fixed. Accordingly, the front surface detector 3 is disposed lateral to the radiation source 2. In other words, the front surface detector 3 is disposed on the same side as that of the radiation source 2 with reference to a virtual plane that passes the position of the object A and is perpendicular to the optical axis X of the radiation source 2. The condenser lens unit 3a of the front surface detector 3 is opposed to the wavelength conversion plate 6. The optical axis 3c of the front surface detector 3 is parallel to the extending direction of the base 10, and is perpendicular to the incidence surface 6a of the wavelength conversion plate 6. In addition, the angle of the optical axis 3c with respect to the incidence surface 6a of the wavelength conversion plate 6 is not limited to the angle described above, and can be appropriately set. It suffices with an arrangement which enables condensing scintillation light emitted from the incidence surface 6a of the wavelength conversion plate 6 by the front surface detector 3. In addition, a light receiving surface of the imaging unit 3b may be substantially parallel to the incidence surface 6a.

Due to the above configuration, the rotating body 20 including the wavelength conversion plate 6, the front surface detector 3, the mirror 5, and the back surface detector 4 is rotatable in an integrated manner centering on the rotation axis L1. That is, the shooting angle changing stage 17 keeps the angle created by the optical axis 3c of the front surface detector 3 and the incidence surface 6a of the wavelength conversion plate 6 at 90 degrees, while rotating the front surface detector 3 and the wavelength conversion plate 6. Further, the shooting angle changing stage 17 keeps the angle created by the optical axis 4c of the back surface detector 4 and the back surface 6b of the wavelength conversion plate 6 at 90 degrees, while rotating the front surface detector 3, the wavelength conversion plate 6, and the back surface detector 4. The shooting angle changing stage 17 changes the angles created by the optical axis 3c of the front surface detector 3 and the optical axis 4c of the back surface detector 4 with respect to the optical axis X of the radiation source 2. With the rotation of the rotating body 20 by the shooting angle changing stage 17, the field of view 23 of the front surface detector 3 and the field of view 24 of the back surface detector 4 also rotate.

As above, because the front surface detector 3, the back surface detector 4, and the wavelength conversion plate 6 rotate in an integrated manner, the relative positional relationship of the front surface detector 3, the wavelength conversion plate 6, and the back surface detector 4 does not change. Therefore, images that are acquired by the front surface detector 3 and the back surface detector 4 are images for which an inter-image operation is easily performed in the image processing device 28. Also, because the angles of the front surface detector 3 and the back surface detector 4 with respect to the wavelength conversion plate 6 are also fixed, it is not necessary to frequently perform calibration in the front surface detector 3 and the back surface detector 4, so that the convenience is high.

The optical axis X of the radiation source 2 fixed on the base 10 creates an angle θ with respect to a normal B to the incidence surface 6a of the wavelength conversion plate 6. That is, the radiation source 2 faces the object A and the incidence surface 6a, and is disposed at a position off the normal B to the incidence surface 6a. In other words, the optical X of the radiation source 2 creates an acute angle with respect to the incidence surface 6a. The angle θ changes with a rotation of the rotating body 20.

Here, the optical axis X of radiation is a straight line connecting the X-ray emission spot 2a of the radiation source 2 and an arbitrary point γ on the incidence surface 6a of the wavelength conversion plate 6. In the present embodiment, the arbitrary point γ is set so as to correspond to a center point of the incidence surface 6a, and in this case, radiation is irradiated relatively evenly. Also, the normal B is a straight line extending from an arbitrary point α on the incidence surface 6a and normal to the incidence surface 6a. In the present embodiment, the arbitrary point α is set so as to correspond to a center point of the incidence surface 6a, and the optical axis X of radiation and the normal B cross each other at the arbitrary point γ (i.e., the arbitrary point α) of the incidence surface 6a. Of course, the arbitrary point γ and the arbitrary point α are not necessarily a center point of the incidence surface 6a, or not necessarily the same point.

The optical axis 3c of the condenser lens unit 3a of the front surface detector 3 is coincident with the normal B to the incidence surface 6a. The front surface detector 3 is capable of imaging scintillation light emitted in the direction of normal B to the incidence surface 6a, and thus easily acquires an image with little perspective. The condenser lens unit 3a focuses on the incidence surface 6a, and condenses scintillation light emitted in the direction of normal B from the incidence surface 6a toward the imaging unit 3b. In addition, the optical axis 3c of the front surface detector 3 may not be coincident with the normal B to the incidence surface 6a.

In this manner, the front surface detector 3 is disposed off the optical axis X of the radiation source 2. That is, the front surface detector 3 is disposed so as to separate from an emission region of radiation from the radiation source 2 (region where a radiation flux 22 exists). Exposure of the front surface detector 3 to radiation from the radiation source 2 is thereby prevented, which prevents a direct conversion signal of radiation from being generated in the interior of the front surface detector 3 to generate noise. Also, the front surface detector 3 is disposed such that a perpendicular line drawn from the center of the condenser lens unit 3a to the incidence surface 6a of the wavelength conversion plate 6 is within the range of the incidence surface 6a, and is disposed over the incidence surface 6a of the wavelength conversion plate 6. A relatively large amount of scintillation light can thereby be detected.

The optical axis 4c of the condenser lens unit 4a of the back surface detector 4 is coincident with a normal C to the back surface 6b via the mirror 5. The back surface detector 4 is capable of imaging scintillation light emitted in the direction of normal C to the back surface 6b, and thus easily acquires an image with little perspective. Here, the normal C is a straight line extending from an arbitrary point β on the back surface 6b and normal to the back surface 6b. Particularly, in the present embodiment, the arbitrary point β is set as a center point of the back surface 6b, the arbitrary point α on the incidence surface 6a and the arbitrary point β on the back surface 6b are located on the same line, and this straight line is coincident with the normal B and the normal C. The condenser lens unit 4a focuses on the back surface 6b, and condenses scintillation light emitted in the direction of normal C from the back surface 6b toward the imaging unit 4b. In addition, the optical axis 4c of the back surface detector 4 may not be coincident with the normal C to the back surface 6b.

In the radiation image acquisition system 1, the optical path length from the incidence surface 6a of the wavelength conversion plate 6 to the front surface detector 3 is equal to the optical path length from the back surface 6b of the wavelength conversion plate 6 to the back surface detector 4. In addition, the optical path length from the incidence surface 6a of the wavelength conversion plate 6 to the front surface detector 3 may be different from the optical path length from the back surface 6b of the wavelength conversion plate 6 to the back surface detector 4. In this case, it is necessary to match the image size etc., by an image processing or the like.

As in the foregoing, because the front surface detector 3, the back surface detector 4, and the wavelength conversion plate 6 rotate in an integrated manner, each of the optical path length from the incidence surface 6a of the wavelength conversion plate 6 to the front surface detector 3 and the optical path length from the back surface 6b of the scintillator 6 to the back surface detector 4 does not change even by a rotation of the rotating body 20, and is fixed. Accordingly, correction to images acquired by each of the front surface detector 3 and the back surface detector 4 is easy.

Subsequently, the operation of the radiation image acquisition system 1 having the configuration described above will then be described. First, control by the timing control unit 27 is performed such that imaging by the front surface detector 3 and imaging by the back surface detector 4 are simultaneously performed. Imaging timing control by the timing control unit 27 allows imaging radiation transmission images of the object A in different energy bands. In detail, a radiation transmission image in a relatively low energy band is imaged by the front surface detector 3, and a radiation transmission image in a relatively high energy band is imaged by the back surface detector 4. Dual-energy imaging is thereby realized. In addition, it is possible in the radiation image acquisition system 1 to control the imaging timings of the front surface detector 3 and the back surface detector 4 so as to be different from each other. Also, the front surface detector 3 and the back surface detector 4 may be controlled so as to be different from each other in the exposure time and number of shots.

Regarding the function of the front surface detector 3 and the back surface detector 4, in other words, fluorescence (scintillation light) converted at the side relatively close to the incidence surface 6a is detected by the front surface detector 3. Detection of fluorescence converted at the incidence surface 6a-side has features that the fluorescence has little blur and the brightness of fluorescence is high. This is because, in front observation, the influence of diffusion and self-absorption in the interior of the wavelength conversion plate 6 can be reduced. On the other hand, in the back surface detector 4, fluorescence converted at the side relatively close to the back surface 6b of the wavelength conversion plate 6 is detected. Also in this case, the influence of diffusion and self-absorption in the interior of the wavelength conversion plate 6 can be reduced.

Next, image signals corresponding to radiation images of both front and back surfaces are output to the image processing device 28 by each of the front surface detector 3 and the back surface detector 4. When the image signals output from each of the front surface detector 3 and the back surface detector 4 are input to the image acquisition unit 28a of the image processing device 28, a predetermined processing such as an inter-image operation including a difference operation and an addition operation is executed based on the input image signals and image signals after the image processing are output to the display device 29 by the image processing unit 28c of the image processing device 28. Then, when the image signals after the image processing output from the image processing device 28 are input to the display device 29, a radiation image according to the input image signals after the image processing is displayed by the display device 29. Particularly, in the image processing device 28, a three-dimensional image of the object A can also be prepared by rotating the object A by the projection angle changing stage 11.

Here, according to the radiation image acquisition system 1 of the present embodiment, an image of the object A can be acquired at a desired magnification ratio, and further, entry of the object A into the field of view 23 of the front surface detector 3 can be prevented. Hereinafter, imaging of the object A by the radiation image acquisition system 1 will be described in greater detail with reference to FIG. 3 to FIG. 6.

As shown in FIG. 3, in a normal shooting state, the object A is disposed within the range of cone beam-shaped X-rays emitted from the radiation source 2 (i.e., within the range of the radiation flux 22). At this time, the front surface detector 3 is disposed such that the field of view 23 of the front surface detector 3 does not include the object A. In this case, as shown in FIG. 6(a), the shot image Pa has a projection image P2a reflected in the luminescent part P1 of the wavelength conversion plate 6. As above, when the object A is shot at a certain level of magnification ratio, vignetting due to the object A is not produced.

Figure 4:
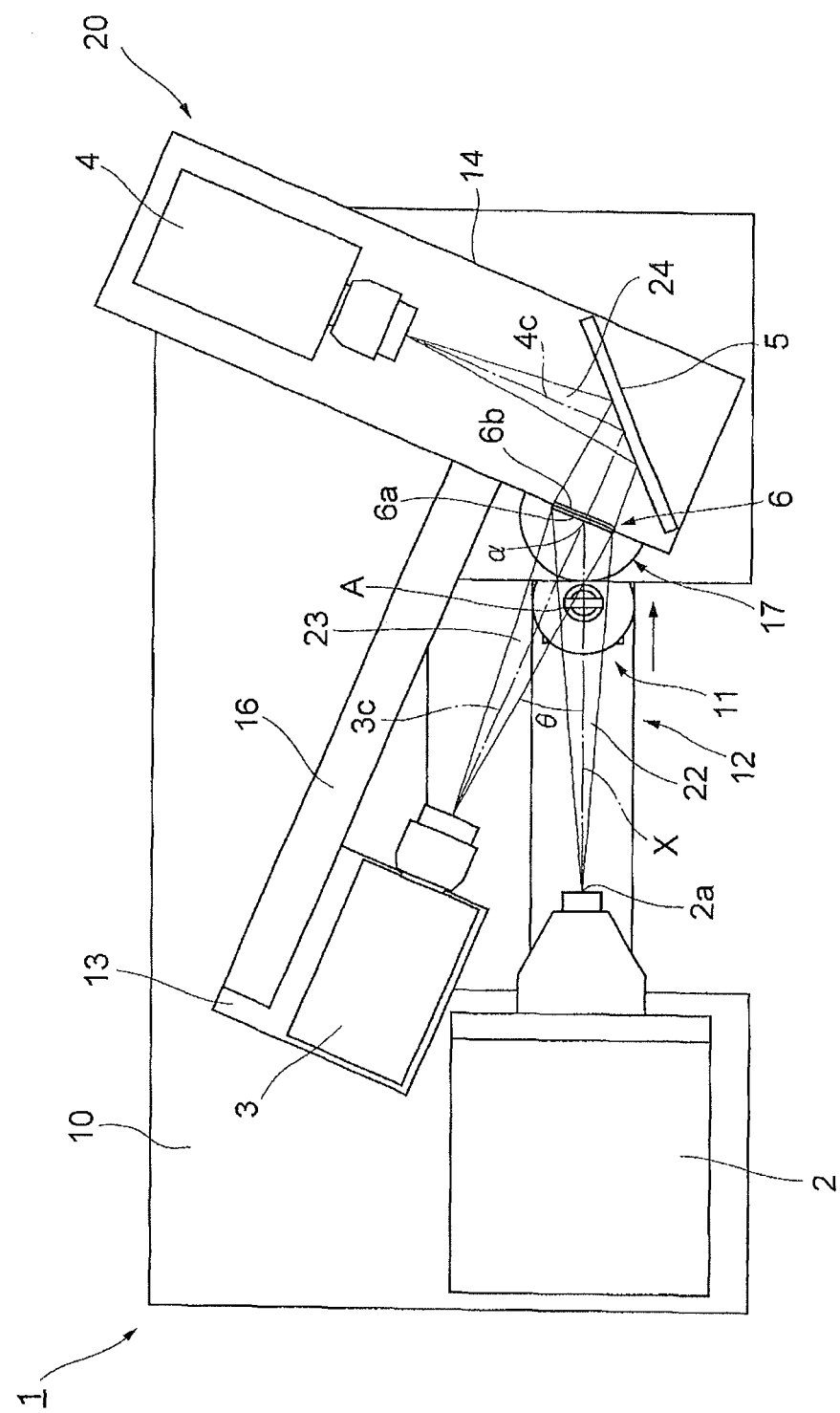
FIG. 4 is a plan view showing a state in which an object is brought close to a wavelength conversion member.

On the other hand, as shown in FIG. 4, when it is desired to change the magnification ratio or the object A cannot be within a cone beam (i.e., within the radiation flux 22) because the sample is large, the object A is moved in a direction to approach the wavelength conversion plate 6 by use of the magnification ratio changing stage 12. At this time, the object A sometimes enters the field of view 23 of the front surface detector 3. In this case, the object A may block light from the wavelength conversion plate 6. Accordingly, as shown in FIG. 6(b), the shot image Pb has not only the projection image P2b but also vignetting P3 due to the object A reflected in the luminescent part P1 of the wavelength conversion plate 6. As above, the object A enters the field of view 23 of the front surface detector 3 when the magnification ratio is lowered, so that vignetting is produced.

Figure 5:
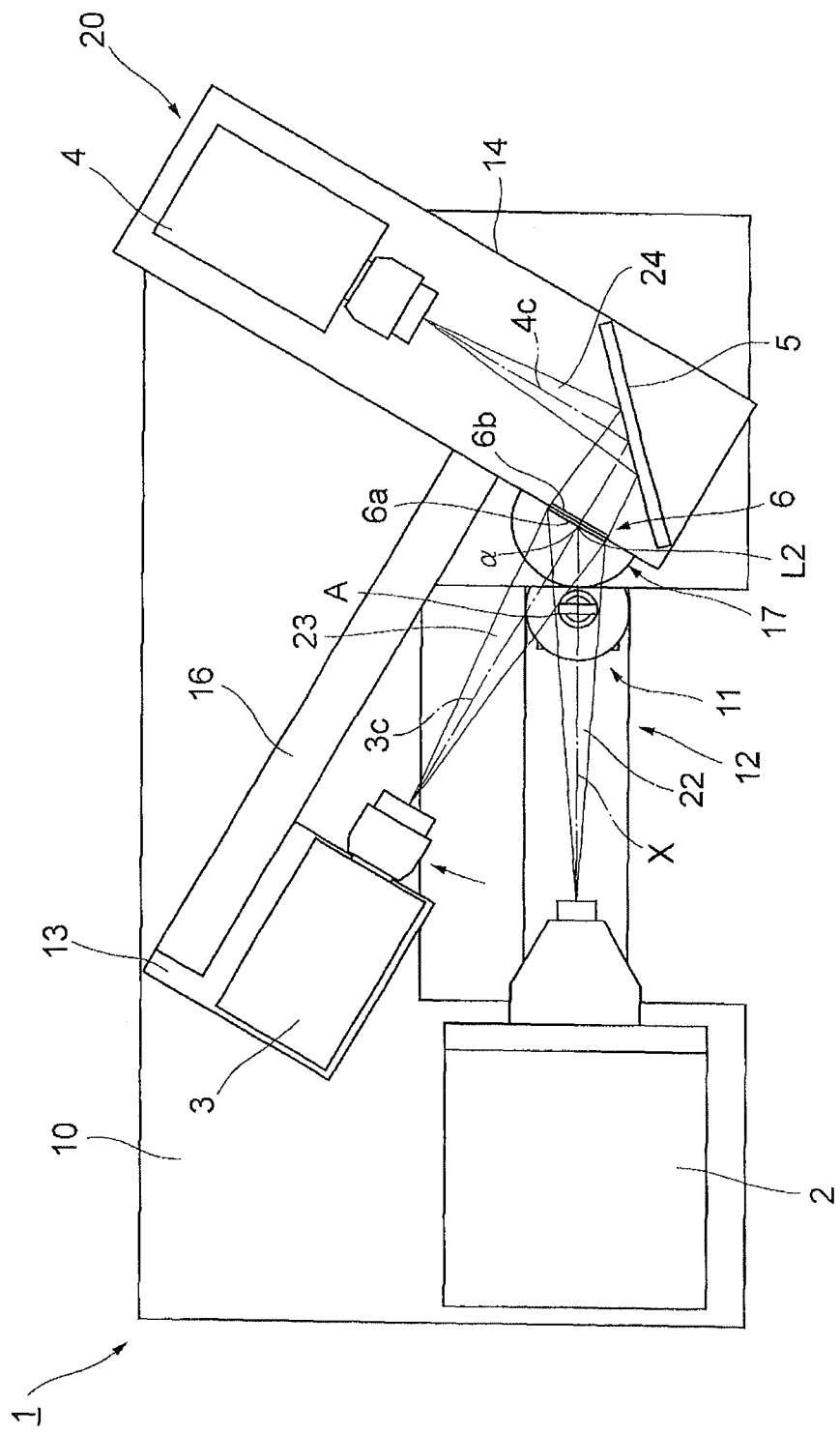
FIG. 5 is a plan view showing a state in which the position of a first imaging means is adjusted.
Figure 6:
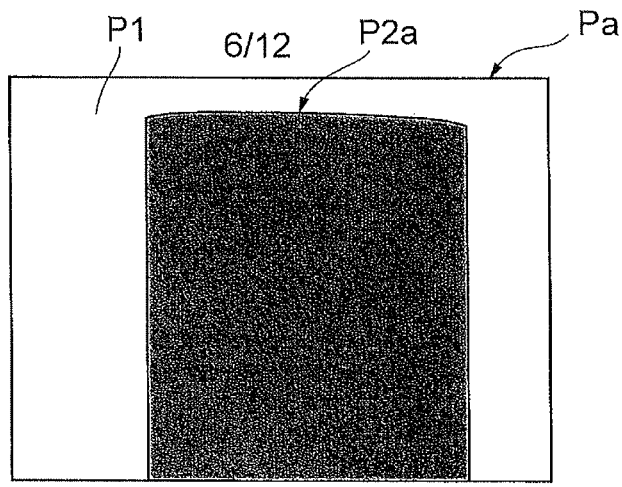
FIG. 6($a$) to FIG. 6($c$) are examples of images captured by the first imaging means.
Figure 6:
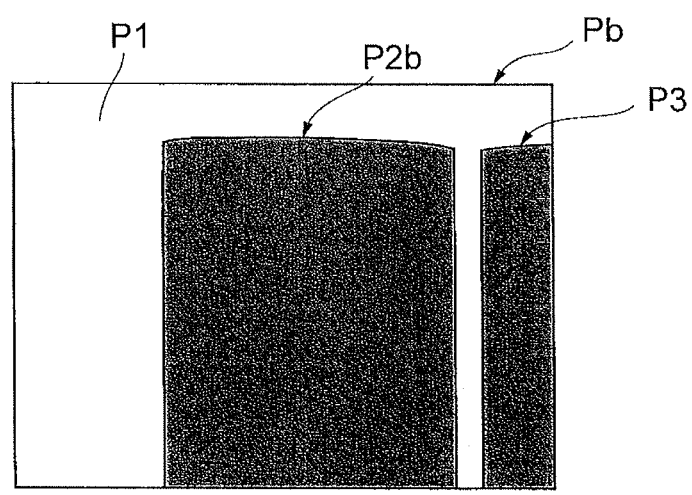
Figure 6:
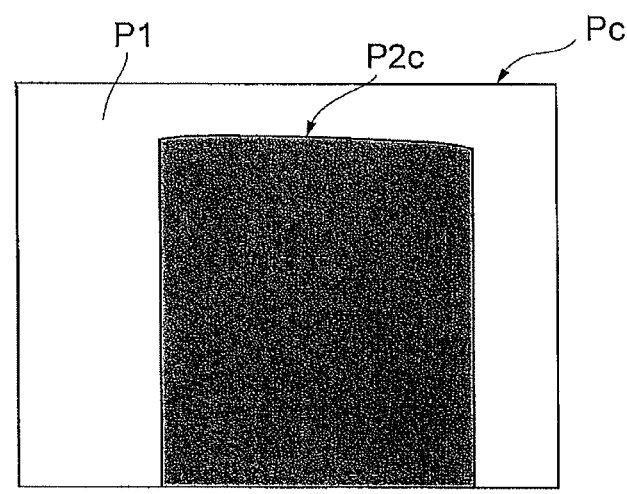

Therefore, as shown in FIG. 5, the X-ray protection box 14 is rotated, by use of the shooting angle changing stage 17, centering on the point α where the optical axis 3c of the front surface detector 3 and the incidence surface 6a of the wavelength conversion plate 6 cross each other (i.e., the rotation axis L2). At this time, with the rotation of the X-ray protection box 14, the front surface detector 3 and the front surface camera mount 13 also rotate with the same rotation center by the same angle through the interlocking arm 16. That is, the rotating body 20 rotates. At this time, because the positional relationship of the front surface detector 3 with the wavelength conversion plate 6 is maintained, it is not necessary to change calibration conditions. As a result of thus moving the front surface detector 3 by rotation, as shown in FIG. 6(c), the shot image Pc has the projection image P2c free from vignetting due to the object A reflected in the luminescent part P1 of the wavelength conversion plate 6. As above, by deepening the camera shooting angle of the front surface detector 3, vignetting due to the object A can be eliminated.

Figure 7:
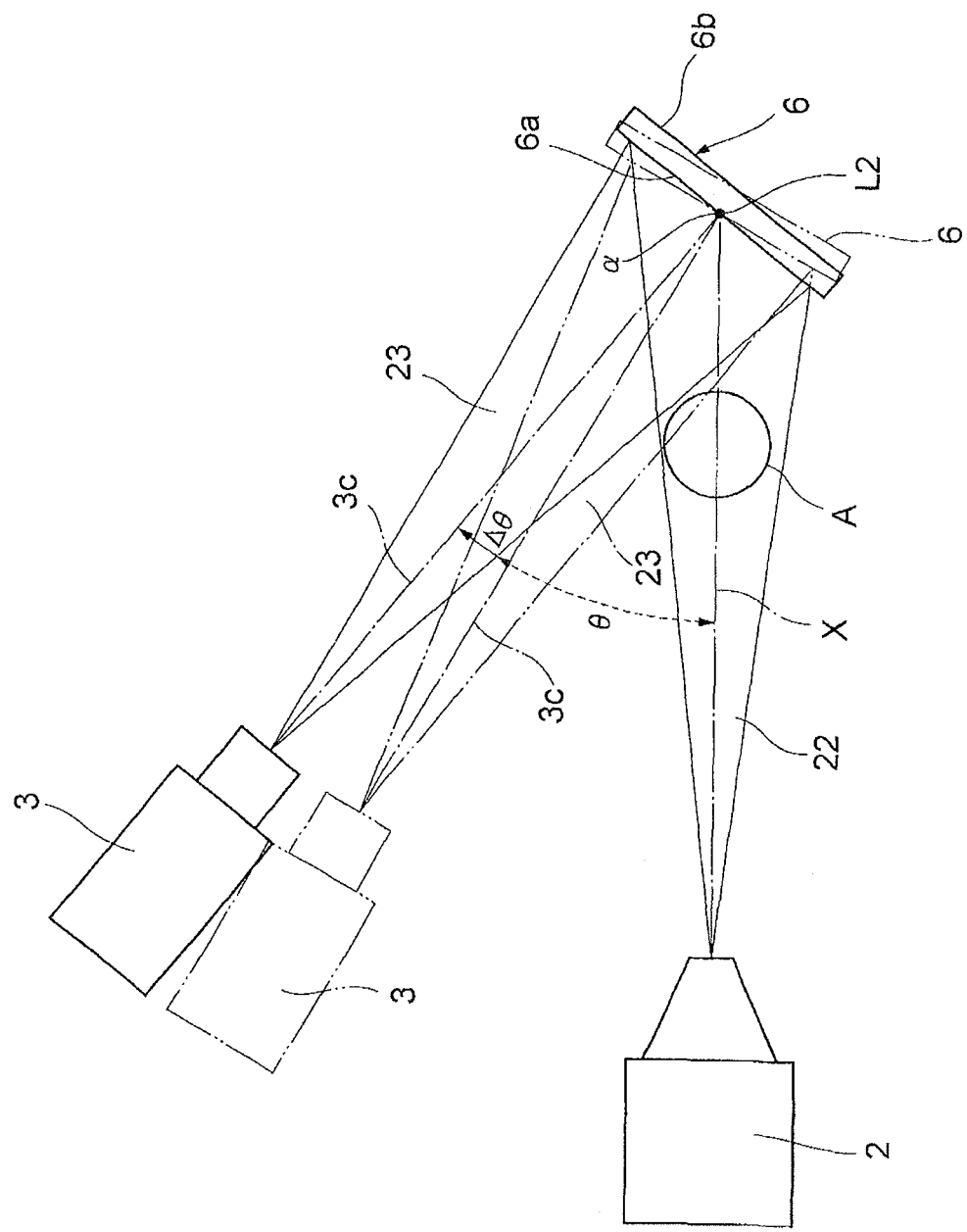
FIG. 7 is an explanatory view showing rotation angles of the first imaging means and wavelength conversion member.

As above, by rotating the front surface detector 3 centering on the rotation axis L2 by the shooting angle changing stage 17, entry of the object A into the field of view 23 of the front surface detector 3 can be prevented. In the example shown in FIG. 7, the object A is removed from the field of view 23 of the front surface detector 3 by further rotating the front surface detector 3 by only an angle Δθ from an angle θ.

In the radiation image acquisition system 1, whether the object A is in the field of view 23 of the front surface detector 3 can be detected by the detection unit 28b of the image processing device 28. The detection unit 28b detects whether the object A is in the field of view 23 of the front surface detector 3 by performing various types of processing to be mentioned below.

Specifically, the detection unit 28b can detect whether the object A is in the field of view 23 of the front surface detector 3 based on an incidence surface image captured by the front surface detector 3 and a back surface image captured by the back surface detector 4.

The detection unit 28b can also detect whether the object A is in the field of view 23 of the front surface detector 3 based on a difference in light intensity between the incidence surface image and the back surface image.

The detection unit 28b can also detect whether the object A is in the field of view 23 of the front surface detector 3 based on a difference image between the incidence surface image and the back surface image.

The detection unit 28b can also detect whether the object A is in the field of view 23 of the front surface detector 3 based on a ratio of brightness between the incidence surface image and the back surface image.

The detection unit 28b can also detect whether the object A is in the field of view 23 of the front surface detector 3 based on successive images of the incidence surface successively captured by the front surface detector 3 while the projection angle changing stage 11 is moved by the magnification ratio changing stage 12.

According to the radiation image acquisition system 1 of the present embodiment described above, scintillation lights emitted from the incidence surface 6a and the back surface 6b of the wavelength conversion plate 6 are respectively condensed and imaged by the front surface detector 3 and the back surface detector 4. By adjusting the position of the projection angle changing stage 11 between the radiation source 2 and the wavelength conversion plate 6 by the magnification ratio changing stage 12, the object A can be brought close to the wavelength conversion plate 6 or moved away from the wavelength conversion plate 6. By bringing the object A close to the wavelength conversion plate 6, the magnification ratio can be lowered. By moving the object A away from the wavelength conversion plate 6 and bringing the object A close to the radiation source 2, the magnification ratio can be increased. Here, even when the object A is brought close to the wavelength conversion plate 6, by adjusting the position of the front surface detector 3 by the shooting angle changing stage 17, entry of the object A into the field of view 23 of the front surface detector 3 can be prevented. Thus, entry of the object A into the field of view 23 of the front surface detector 3 being an imaging means on the incidence surface side can be prevented, while an image can be acquired at a desired magnification ratio. Also, the occurrence of vignetting due to the object A can be prevented.

Because the shooting angle changing stage 17 rotates the front surface detector 3 with the point α where the optical axis 3c of the front surface detector 3 and the incidence surface 6a of the wavelength conversion plate 6 cross each other set as a rotation center, even when the position of the front surface detector 3 is adjusted, the optical path length from the wavelength conversion plate 6 to the front surface detector 3 does not change. Accordingly, correction to an image is easy.

Even when the position of the front surface detector 3 is adjusted, the angle created by the optical axis 3c of the front surface detector 3 and the incidence surface 6a of the wavelength conversion plate 6 is kept fixed, and thus correction to an image becomes even easier. Also, it is not necessary to frequently perform calibration in the front surface detector 3, so that the convenience is improved.

The front surface detector 3, the wavelength conversion plate 6, and the back surface detector 4 integrally rotate with the point α described above set as a rotation center. Accordingly, even when the position of the front surface detector 3 and the back surface detector 4 is adjusted, the relative positional relationship of the front surface detector 3, the wavelength conversion plate 6, and the back surface detector 4 does not change. Therefore, images for which an inter-image operation is easily performed can be captured. Also, it is not necessary to frequently perform calibration in the back surface detector 4, so that the convenience is improved.

Conventionally, when the object A is large-sized or has a low magnification ratio (i.e., the object A is close to the wavelength conversion plate 6), the object A overlaps the field of view 23 of the front surface detector 3, and the shootable area has consequently been limited. According to the radiation image acquisition system 1, the shootable area can be widened by widening the angle range in which the optical axis 3c can be moved.

By making the angle created by the optical axis X of the radiation source 2 and the optical axis 3c of the front surface detector 3 to a minimum when the object A is small, the influence of "vignetting" due to an inclination of the wavelength conversion plate 6 can be reduced, and a loss or decline in resolution can be reduced as much as possible.

Because whether the object A is in the field of view 23 of the front surface detector 3 is detected by the detection unit 28b, the occurrence of vignetting in an image can be reliably prevented.

The detection unit 28b detects whether the object A is in the field of view 23 of the front surface detector 3 based on an incidence surface image captured by the front surface detector 3 and a back surface image captured by the back surface detector 4. This allows accurately detecting whether the object A is in the field of view 23.

The detection unit 28b can also detect whether the object A is in the field of view 23 of the front surface detector 3 based on a difference in light intensity between the incidence surface image and the back surface image. This allows accurately detecting whether the object A is in the field of view 23.

The detection unit 28b can also detect whether the object A is in the field of view 23 of the front surface detector 3 based on a difference image between the incidence surface image and the back surface image. This allows accurately detecting whether the object A is in the field of view 23.

The detection unit 28b can also detect whether the object A is in the field of view 23 of the front surface detector 3 based on successive images of the incidence surface successively captured by the front surface detector 3 while the projection angle changing stage 11 is moved by the magnification ratio changing stage 12. This allows accurately detecting the point in time where the object A has slipped out of the field of view 23 of the front surface detector 3 or the point in time where the object A has entered the field of view 23 of the front surface detector 3. As a result, the inclination angle of the wavelength conversion plate 6 with respect to the radiation source 2 can be minimized, so that an image with little perspective is easily acquired.

Meanwhile, when the radiation image acquisition system 1 is an X-ray CT system, information on the angles with respect to the optical axis X of the radiation source 2 and the incidence surface 6a of the wavelength conversion plate 6 becomes necessary. In the radiation image acquisition system 1, because the angle of the incidence surface 6a of the wavelength conversion plate 6 and the optical axis 3c of the front surface detector 3 is kept fixed, by determining the angle of the optical axis X of the radiation source 2 and the optical axis 3c of the front surface detector 3, a CT image can be acquired.

Figure 8:
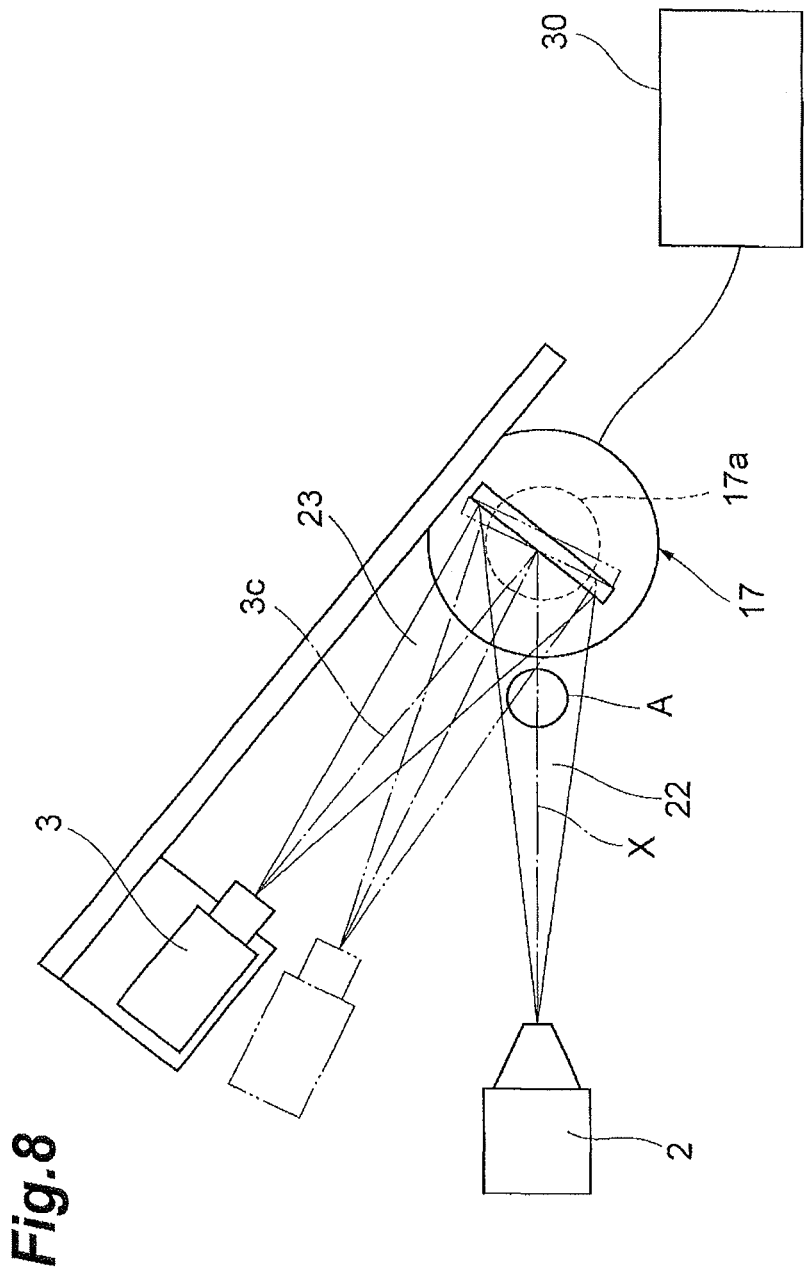
FIG. 8 is a view showing an angle changing method by drive of a rotation actuator.

Specifically, as shown in FIG. 8, the angle can be changed by driving the drive mechanism 17a that is a rotation actuator. In this case, a shot image is checked (visual or algorithmic detection is performed), and the angle of the front surface detector 3 is changed to reach a position where the object A is not reflected in the image. Then, the angle at that time is detected. Changing the angle of the wavelength conversion plate 6 and the front surface detector 3 by the drive mechanism 17a allows obtaining the changed angle by, for example, a PC 30 connected to the drive mechanism 17a. The angle between the optical axis X and the optical axis 3c can thereby be obtained.

Figure 9:
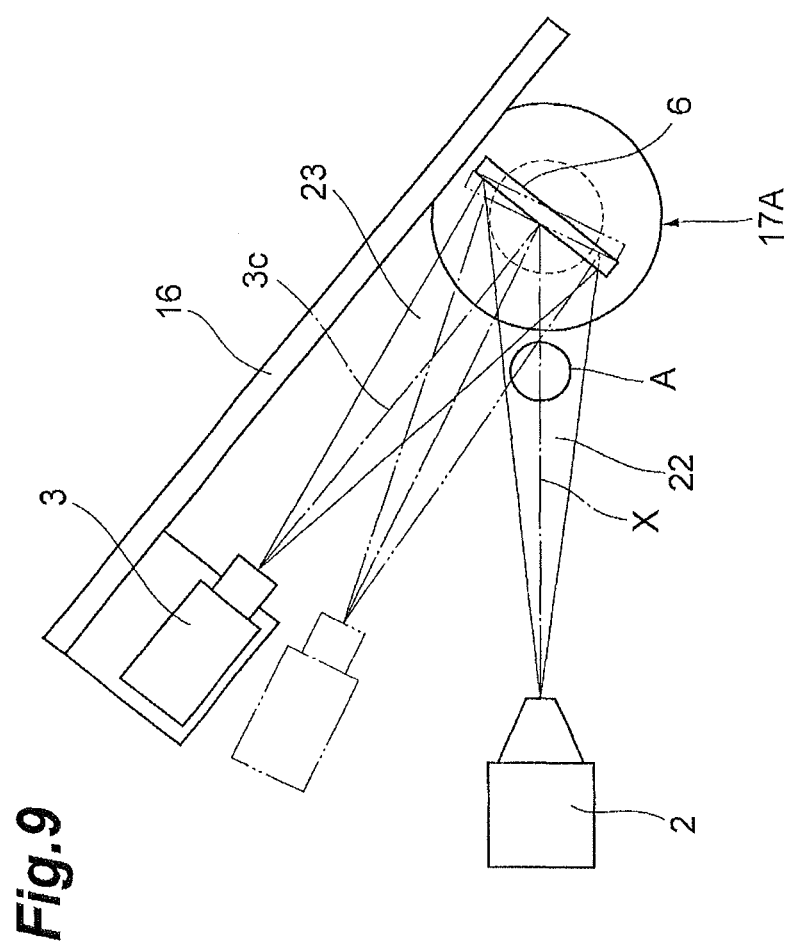
FIG. 9 is a view showing a manual angle changing method.

Also, as shown in FIG. 9, the angle can also be manually changed. In this case, by disposing the wavelength conversion plate 6 and the front surface detector 3 on a graduated rotating stage (imaging position adjusting means) 17A and reading the graduation when the angle was manually changed, the angle between the optical axis X and the optical axis 3c can be obtained.

In these cases, the image processing unit 28c of the image processing device 28 can perform an image operation of the incidence surface image and the back surface image based on a rotation angle of the front surface detector 3, the wavelength conversion plate 6, and the back surface detector 4. According to the image processing device 28 including the image processing unit 28c, a CT image of the object A can be acquired.

Figure 10:
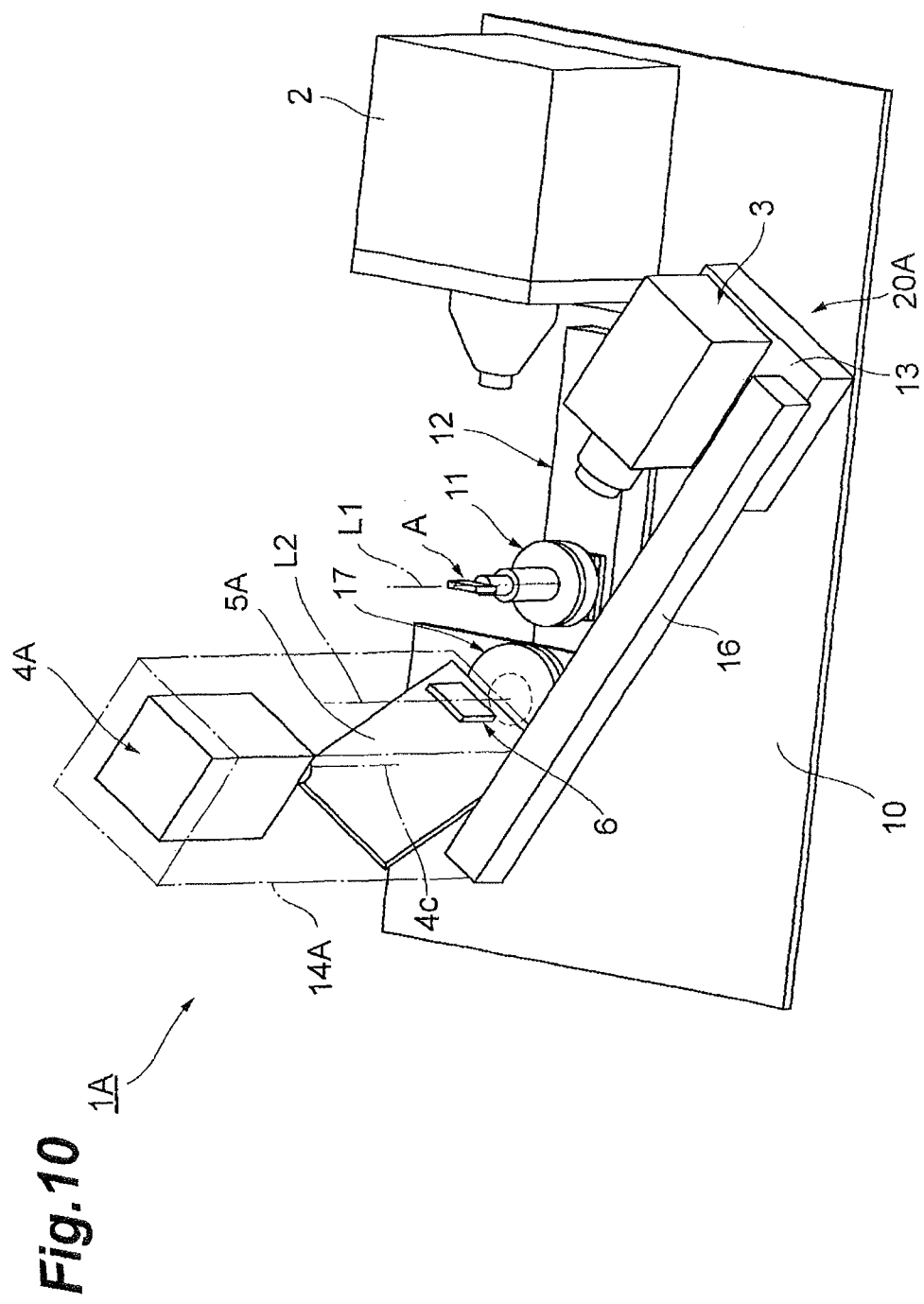
FIG. 10 is a perspective view of a radiation image acquisition system according to a second embodiment.
Figure 11:
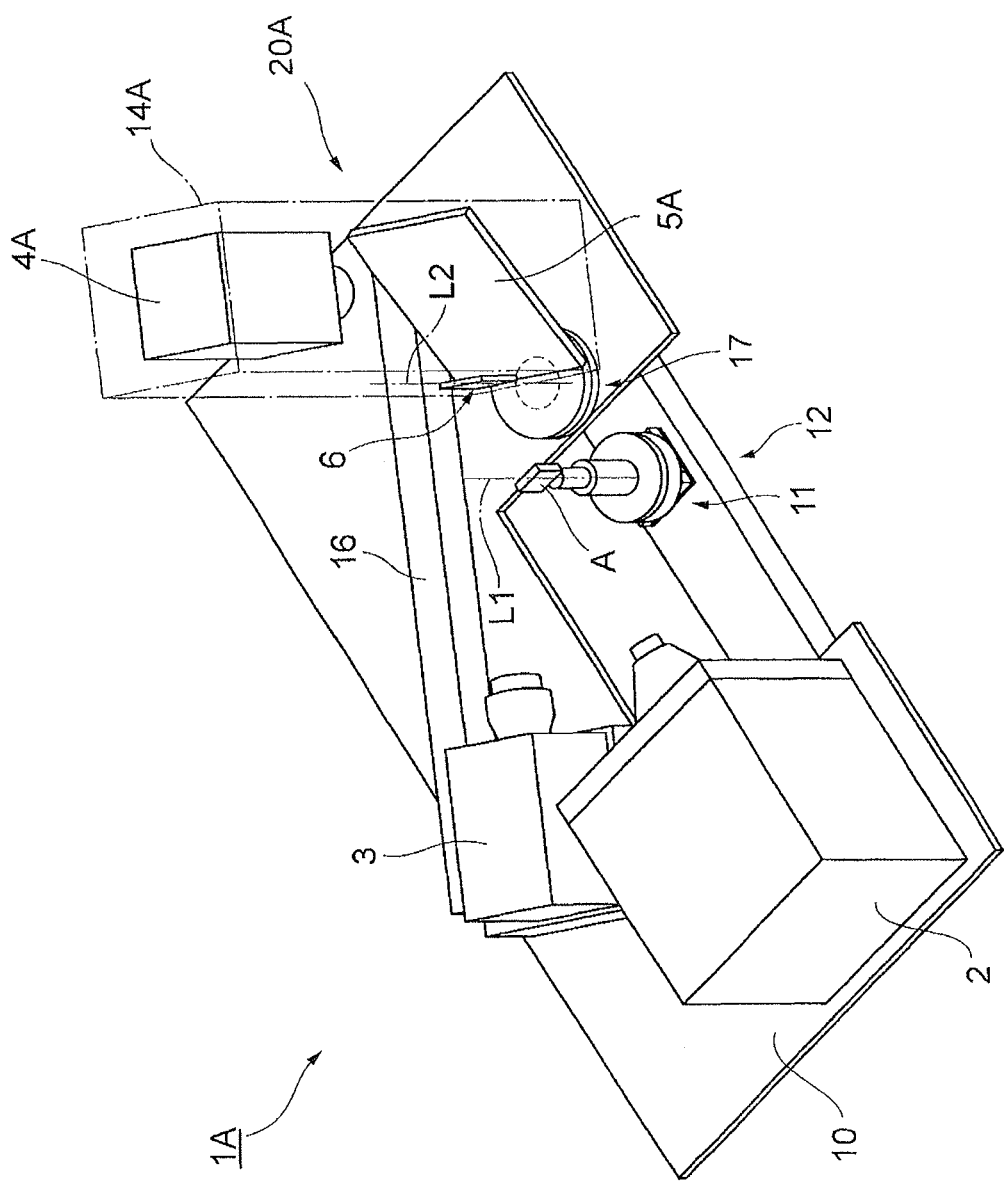
FIG. 11 is a perspective view of the radiation image acquisition system of FIG. 10 from another angle.

Next, a radiation image acquisition system 1A of a second embodiment will be described with reference to FIG. 10 to FIG. 12. The difference in the radiation image acquisition system 1A shown in FIG. 10 to FIG. 12 from the radiation image acquisition system 1 of the first embodiment is the point of adopting a rotating body 20A having a vertical X-ray protection box 14A in place of the rotating body 20 having the horizontal X-ray protection box 14. In the vertical X-ray protection box 14A, the disposition itself of the wavelength conversion plate 6 has not been changed from that of the radiation image acquisition system 1, but the disposition of a mirror 5A and a back surface detector 4A has been changed. That is, the optical axis 4c of the back surface detector 4A is perpendicular to the extending direction of the base 10. The mirror 5A has a reflecting surface that is inclined at 45 degrees with respect to the extending direction of the base 10. In addition, similar to the radiation image acquisition system 1, the radiation image acquisition system 1A also includes a timing control unit 27, an image processing device 28, and a display device 29.

Also according to such a radiation image acquisition system 1A, the position of the front surface detector 3 can be adjusted by rotating the rotating body 20A centering on the rotation axis L2. Thus, the same advantageous effects as those of the radiation image acquisition system 1 can be provided.

As above, the embodiment of the present invention has been described, but the present invention is not limited to the above-described embodiment. In the above-described embodiment, a description has been given of the case where the front surface detector 3 rotates centering on the rotation axis L2, but the front surface detector 3 may rotate centering on another rotation axis. The other rotation axis may pass an intersection of the optical axis 3c of the front surface detector 3 and the incidence surface 6a of the wavelength conversion plate 6, but may not pass the intersection. The movement of the front surface detector 3 is not limited to a rotational movement, and may be a sliding movement. Whether the object A is in the field of view 23 of the front surface detector 3 may be detected by other means. For example, a dedicated detector may be used separately.

INDUSTRIAL APPLICABILITY

According to an aspect of the present invention, entry of an object into the field of view of the first imaging means being an imaging means on the incidence surface side can be prevented, while an image can be acquired at a desired magnification ratio.

REFERENCE SIGNS LIST 1, 1A . . . radiation image acquisition system, 2 . . . radiation source (radiation source), 3 . . . front observation photodetector (first imaging means), 3c . . . optical axis, 4 . . . back observation photodetector (second imaging means), 4c . . . optical axis, 6 . . . wavelength conversion plate (wavelength conversion member), 6a . . . incidence surface, 6b . . . back surface (surface on the opposite side), 11 . . . projection angle changing stage (holding unit), 12 . . . magnification ratio changing stage (holding unit position adjusting means), 17 . . . shooting angle changing stage (imaging position adjusting means), 23 . . . field of view (field of view of first imaging means), 28b . . . detection unit (detecting means), 28c . . . image processing unit (image operating means), A . . . object, α . . . point.

The invention claimed is:

1. A system for acquiring a radiation image of an object, the system comprising:
a radiation source configured to emit radiation toward the object;
a holder configured to hold the object;
a wavelength conversion member configured to generate scintillation light in response to incidence of the radiation transmitted through the object;
a first imaging device configured to condense and image scintillation light emitted from an incidence surface of the wavelength conversion member;
a second imaging device configured to condense and image scintillation light emitted from a surface opposite to the incidence surface of the wavelength conversion member;
a holder position adjusting device configured to adjust a position of the holder between the radiation source and the wavelength conversion member; and
an imaging position adjusting device configured to adjust a position of the first imaging device.

2. The system according to claim 1, wherein the imaging position adjusting device rotates the first imaging device with a point where an optical axis of the first imaging device and the incidence surface of the wavelength conversion member cross each other set as a rotation center.

3. The system according to claim 2, wherein the imaging position adjusting device keeps an angle created by the optical axis of the first imaging device and the incidence surface of the wavelength conversion member while rotating the first imaging device and the wavelength conversion member.

4. The system according to claim 3, wherein the imaging position adjusting device keeps an angle created by an optical axis of the second imaging device and the opposite surface of the wavelength conversion member while rotating the first imaging device, the wavelength conversion member, and the second imaging device.

5. The system according to claim 4, further comprising an image operating device configured to perform an image operation of a first image captured by the first imaging device and a second image captured by the second imaging device based on a rotation angle of the first imaging device, the wavelength conversion member, and the second imaging device.

6. The system according to claim 4, further comprising a detecting device configured to detect whether the object is in a field of view of the first imaging device.

7. The system according to claim 6, further comprising an image operating device configured to perform an image operation of a first image captured by the first imaging device and a second image captured by the second imaging device based on a rotation angle of the first imaging device, the wavelength conversion member, and the second imaging device.

8. The system according to claim 6, wherein the detecting device detects whether the object is in the field of view of the first imaging device based on a first image captured by the first imaging device and a second image captured by the second imaging device.

9. The system according to claim 8, wherein the detecting device detects whether the object is in the field of view of the first imaging device based on a difference in light intensity between the first image and the second image.

10. The system according to claim 9, further comprising an image operating device configured to perform an image operation of a first image captured by the first imaging device and a second image captured by the second imaging device based on a rotation angle of the first imaging device, the wavelength conversion member, and the second imaging device.

11. The system according to claim 8, wherein the detecting device detects whether the object is in the field of view of the first imaging device based on a difference image between the first image and the second image.

12. The system according to claim 11, further comprising an image operating device configured to perform an image operation of a first image captured by the first imaging device and a second image captured by the second imaging device based on a rotation angle of the first imaging device, the wavelength conversion member, and the second imaging device.

13. The system according to claim 8, wherein the detecting device detects whether the object is in the field of view of the first imaging device based on a ratio of brightness between the first image and the second image.

14. The system according to claim 13, further comprising an image operating device configured to perform an image operation of a first image captured by the first imaging device and a second image captured by the second imaging device based on a rotation angle of the first imaging device, the wavelength conversion member, and the second imaging device.

15. The system according to claim 8, wherein the detecting device detects whether the object is in the field of view of the first imaging device based on successive images successively captured by the first imaging device while the holder is moved by the holder position adjusting device.

16. The system according to claim 15, further comprising an image operating device configured to perform an image operation of a first image captured by the first imaging device and a second image captured by the second imaging device based on a rotation angle of the first imaging device, the wavelength conversion member, and the second imaging device.

17. The system according to claim 8, further comprising an image operating device configured to perform an image operation of a first image captured by the first imaging device and a second image captured by the second imaging device based on a rotation angle of the first imaging device, the wavelength conversion member, and the second imaging device.

* * * * *